United States Patent
Basu et al.

(10) Patent No.: US 7,881,426 B2
(45) Date of Patent: Feb. 1, 2011

(54) METHOD AND SYSTEM FOR PERFORMING A SCAN OF AN OBJECT

(75) Inventors: Samit Kumar Basu, Fremont, CA (US); Jian Gao, San Jose, CA (US); Steven Leslie Hills, San Jose, CA (US); Eugene Alex Ingerman, San Francisco, CA (US); Pierfrancesco Landolfi, Palo Alto, CA (US); Sussan Pourjavid-Granfors, Sunnyvale, CA (US)

(73) Assignee: Morpho Detection, Inc., Newark, CA (US)

( * ) Notice: Subject to any disclaimer, the term of this patent is extended or adjusted under 35 U.S.C. 154(b) by 105 days.

(21) Appl. No.: 12/393,591

(22) Filed: Feb. 26, 2009

(65) Prior Publication Data

US 2010/0215144 A1     Aug. 26, 2010

(51) Int. Cl.
*A61B 6/03* (2006.01)
*H05G 1/30* (2006.01)
*G01N 23/083* (2006.01)

(52) U.S. Cl. ............... 378/20; 378/15; 378/57; 378/98.12

(58) Field of Classification Search ............ 378/15, 378/20, 57, 98.12
See application file for complete search history.

(56) References Cited

U.S. PATENT DOCUMENTS

| | | | |
|---|---|---|---|
| 5,901,198 A | 5/1999 | Crawford et al. | |
| 5,949,842 A | 9/1999 | Schafer et al. | |
| 5,970,113 A | 10/1999 | Crawford et al. | |
| 6,185,272 B1 | 2/2001 | Hiraoglu et al. | |
| 6,236,706 B1 * | 5/2001 | Hsieh | 378/8 |
| 6,256,404 B1 | 7/2001 | Gordon et al. | |
| 6,430,255 B2 | 8/2002 | Fenkart et al. | |
| 7,050,536 B1 | 5/2006 | Fenkart et al. | |
| 7,203,267 B2 | 4/2007 | De Man et al. | |
| 7,280,632 B2 * | 10/2007 | Katsevich | 378/15 |
| 7,313,216 B2 * | 12/2007 | Nishide et al. | 378/15 |
| 7,403,587 B2 * | 7/2008 | Bontus et al. | 378/4 |
| 7,421,057 B2 * | 9/2008 | Watanabe | 378/8 |
| 7,428,290 B2 * | 9/2008 | Nishide et al. | 378/4 |

(Continued)

OTHER PUBLICATIONS

L.A. Feldkamp, et al; "Practical Cone-Beam Algorithm"; J. Opt. Soc. Am. A/vol. 1, No. 6/ Jun. 1984.

(Continued)

*Primary Examiner*—Allen C. Ho
(74) *Attorney, Agent, or Firm*—Armstrong Teasdale LLP (57) ABSTRACT

A method for generating an image of an object using a scanning system includes performing a first portion of a scan in a first scanning mode to acquire a first dataset, receiving a halt command for a conveyor within the scanning system, decelerating the conveyor to a halt based on the halt command using a conveyor controller, and, when the object is present within an examination region after the conveyor has halted, performing a second portion of the scan in a second scanning mode to acquire a second dataset. The second scanning mode is different than the first scanning mode. The method also includes reconstructing the first dataset using a first reconstruction algorithm and reconstructing the second dataset using a second reconstruction algorithm. The second reconstruction algorithm is different than the first reconstruction algorithm. The image is generated using the first reconstructed dataset and the second reconstructed dataset.

20 Claims, 5 Drawing Sheets

U.S. PATENT DOCUMENTS

| | | | |
|---|---|---|---|
| 7,492,860 B2 * | 2/2009 | Garms et al. | 378/57 |
| 7,522,696 B2 * | 4/2009 | Imai | 378/8 |
| 7,522,697 B2 * | 4/2009 | Satta et al. | 378/15 |
| 7,639,776 B2 * | 12/2009 | Gohno et al. | 378/15 |
| 7,724,866 B2 * | 5/2010 | Naidu et al. | 378/15 |
| 7,756,240 B2 * | 7/2010 | Nishide et al. | 378/5 |
| 7,778,381 B2 * | 8/2010 | Nishide et al. | 378/4 |

OTHER PUBLICATIONS

Alexander Katsevich, et al; "Exact Filtered Back Projection Reconstruction for Dynamic Pitch Helical Cone Beam Computed Tomography"; Institute of Physics Publishing; Physics in Medicine and Biology; 49 (2004) 3089-3103.

* cited by examiner

METHOD AND SYSTEM FOR PERFORMING A SCAN OF AN OBJECT

BACKGROUND OF THE INVENTION

1. Field of the Invention

The embodiments described herein relate generally to a scanning system for scanning a stream of objects and, more particularly, to a scanning system for scanning a stream of objects that halts and resumes motion.

2. Description of the Related Art

At least some known scanning systems use a computer tomography (CT) system as an imaging section of the scanning system to scan a stream of objects. At least some known volumetric CT systems use helical scan protocols. However, proper image reconstruction using a helical scan protocol with a stream of objects generally requires that objects being scanned move at a constant velocity through the CT system. In at least some applications, for example, in scanning of airline luggage, it may become necessary to halt the stream of objects while being conveyed through the CT system. Such halting is also referred to as "die-back." After a time period, the scanning of the stream of objects resumes. However, during the halting of the stream of objects, and subsequent acceleration from the halt, the constant speed assumption used for image reconstruction under the helical scan protocol is violated. Accordingly, during halting and acceleration conditions, at least some known CT systems are unable to scan and reconstruct an object within the stream of objects properly.

One known scanning system that includes a CT system does not scan a stream of objects and, as such, does not require the constant velocity assumption to reconstruct images of each object. Accordingly, halting the stream of objects within the scanning system does not adversely affect image reconstruction. However, when a stream of objects is not scanned, throughput of the scanning system may be reduced. Another known scanning system that includes a CT system generates three-dimensional images by scanning a stream of objects. In such a scanning system, when the stream of objects is halted, data acquired regarding an object within the CT system is discarded and the entire object is manually inspected. However, manually inspecting objects may be time consuming and costly.

Accordingly, there is a need for a scanning system that can scan a stream of objects and reconstruct an image of an object within the stream even if the stream of objects is halted and accelerated while the object is within an imaging section of the scanning system and a scan is being performed.

BRIEF SUMMARY OF THE INVENTION

In one aspect, a method for generating an image of an object using a scanning system is provided. The method includes performing a first portion of a scan in a first scanning mode to acquire a first dataset using a scan controller, receiving a halt command for a conveyor within the scanning system at at least a conveyor controller, decelerating the conveyor to a halt based on the halt command using the conveyor controller, and, when the object is present within an examination region after the conveyor has halted, performing a second portion of the scan in a second scanning mode to acquire a second dataset using the scan controller. The second scanning mode is different than the first scanning mode. The method also includes reconstructing the first dataset using a first reconstruction algorithm within a control system and reconstructing the second dataset using a second reconstruction algorithm within the control system. The second reconstruction algorithm is different than the first reconstruction algorithm. The image is generated by the control system using the first reconstructed dataset and the second reconstructed dataset.

In another aspect, a scanning system is provided. The scanning system includes a conveyor configured to convey a stream of objects through the scanning system, a conveyor controller in operative control communication with the conveyor, a computer tomography (CT) system, a scan controller in operative control communication with the CT system, and a control system in communication with the conveyor controller and the scan controller. The control system is configured to perform a first portion of a scan in a first scanning mode to acquire a first dataset using the scan controller, issue a halt command to at least the conveyor controller, decelerate the conveyor to a halt based on the halt command using the conveyor controller, and, when an object is present within an examination region after the conveyor has halted, perform a second portion of the scan in a second scanning mode to acquire a second dataset using the scan controller. The second scanning mode is different than the first scanning mode. The control system is also configured to reconstruct the first dataset using a first reconstruction algorithm and reconstruct the second dataset using a second reconstruction algorithm. The second reconstruction algorithm is different than the first reconstruction algorithm. An image is generated using the first reconstructed dataset and the second reconstructed dataset.

The embodiments described herein scan a stream of objects and reconstruct an image of an object within the stream even if the stream of objects is halted and accelerated while the object is within an imaging section of the scanning system and a scan is being performed. Further, data acquired prior to the halt is used to reconstruct the image of the object rather than discarded.

BRIEF DESCRIPTION OF THE DRAWINGS

FIGS. 1-4 show exemplary embodiments of the system and method described herein.

DETAILED DESCRIPTION OF THE INVENTION

In order to accurately inspect and reconstruct an image of an object within an imaging section of a scanning system when a halt/dieback situation occurs, a method of scanning an object includes scanning an object using a first scanning mode and, after a halt/dieback situation occurs, scanning the object using a second mode. Hereinafter, the term "halt/dieback" is referred to as a "halt" and/or "halting." Data from the first scanning mode is reconstructed using a first reconstruction algorithm, and data from the second scanning mode is reconstructed using a second reconstruction algorithm. Such a method may be implemented using any suitable scanning methods.

Three example implementations include: (1) a first implementation that includes recording a motion of a conveyor as an object is accelerated, and using this recorded motion to modify a reconstruction algorithm for the second scanning mode; (2) a second implementation includes scanning an object in an imaging section in a "step-and-shoot" mode after resuming motion and accelerating the conveyor to full speed after the object exits the imaging section; and (3) a third implementation includes scanning an object in an imaging section at a reduced constant velocity after motion is resumed until the object exits the imaging section. In each of the three examples, the scanning system is configured to perform a different reconstruction technique during a time in which an object within the imaging section resumes motion.

As used herein, the phrase "reconstructing an image" is not intended to exclude embodiments in which data representing an image is generated but a viewable image is not. Therefore, as used herein the term "image" broadly refers to both viewable images and data representing a viewable image. However, many embodiments generate (or are configured to generate) at least one viewable image. Additionally, although described in detail in a CT inspection setting, it is contemplated that the benefits accrue to all imaging modalities including, for example, ultrasound, Magnetic Resonance Imaging (MRI), Electron Beam CT (EBCT), Positron Emission Tomography (PET), Single Photon Emission Computed Tomography (SPECT), and in both non-medical settings and medical settings. Further, as used herein, "a scan" refers to a continuous scan that begins when a first object of a stream of objects enters a scanning system and ends when a last object of the stream of objects exits the scanning system.

In the embodiments described herein, a scanning mode of the scan is switched between a first scanning mode and a second mode while the scan is continuously performed. More specifically, when a conveyor halts during the continuous scan, a scanning mode of the scan switches from the first scanning mode to the second scanning mode. After an object has cleared an imaging section after the halt, the scanning mode of the scan switches from the second scanning mode back to the first scanning mode. During the scanning mode switches, even if the conveyor halts, the scan continues to be performed.

Figure 1:
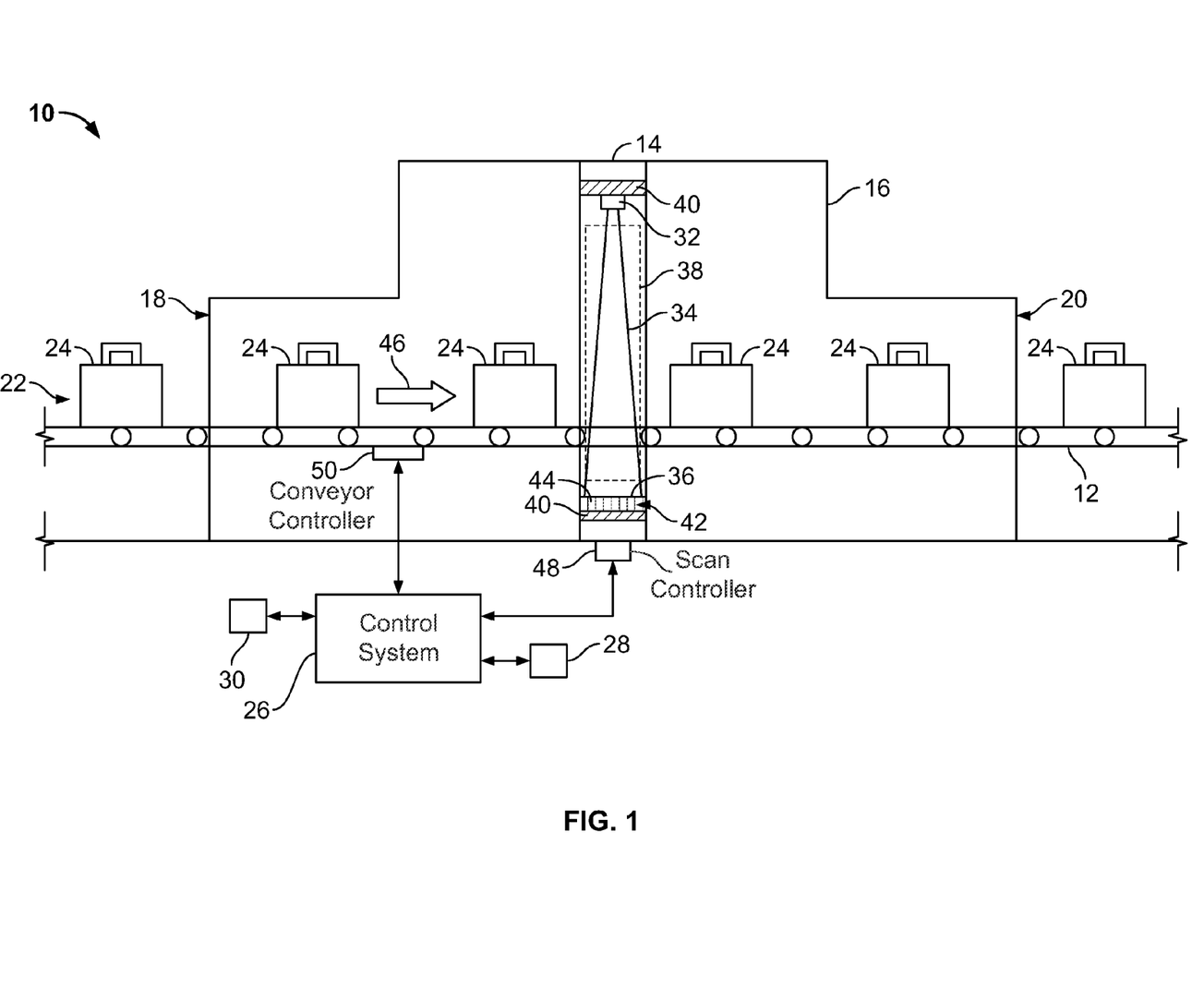
FIG. 1 is a schematic, partial sectional view of an exemplary scanning system.

FIG. 1 is a schematic view of an exemplary scanning system 10. Scanning system 10 includes a conveyor 12 and an imaging section or a CT system 14 positioned at least partially within a housing 16. CT system 14 may also be referred to herein as an imaging section of scanning system 10. Conveyor 12 extends between an inlet 18 of housing 16 and an outlet 20 of housing 16. Further, conveyor 12 is configured to transport a stream 22 of objects 24 through scanning system 10. In the exemplary embodiment, stream 22 includes at least one object 24. Conveyor 12 extends through CT system 14 and conveys objects 24 sequentially through CT system 14 such that each object 24 is scanned by CT system 14. CT system 14 is configured to scan objects 24 one at a time in the exemplary embodiment.

A control system 26 is in operational control communication with conveyor 12 and CT system 14. As used herein, "operational control communication" refers to a link, such as a conductor, a wire, and/or a data link, between two or more components of scanning system 10 that enables signals, electric currents, and/or commands to be communicated between the two or more components. The link is configured to enable one component to control an operation of another component of scanning system 10 using the communicated signals, electric currents, and/or commands. Further, as used herein, the term "control system" is not limited to just those integrated circuits referred to in the art as a control system, but broadly refers to a computer, microcontroller, a microcomputer, a programmable logic controller, an application specific integrated circuit, and/or any other programmable circuit.

Control system 26 includes a central processing unit and may include a device, such as a floppy disk drive or a compact-disc read-only memory (CD-ROM) drive, for reading data from a computer-readable medium, such as a floppy disk, a compact disc-read only memory (CD-ROM), a magneto-optical disk (MOD), and/or a digital versatile disc (DVD). In an alternative embodiment, control system 26 executes instructions stored in firmware. In the exemplary embodiment, control system 26 controls speed, acceleration, deceleration, starting, stopping, and/or any other suitable function of conveyor 12. Further, control system 26 controls CT system 14 and/or conveyor 12 to acquire data relating to objects 24, as described in more detail below. In the exemplary embodiment, control system 26 is also in communication with an input device 28 and a display device 30. Display device 30 may include, without limitation, a liquid crystal display (LCD), a cathode ray tube (CRT), and/or any other suitable output device. Input device 28 includes, without limitation, a mouse and a keyboard.

In the exemplary embodiment, CT system 14 includes a radiation source 32 for emitting radiation 34 and a detector 36 for detecting emitted radiation 34. An examination region 38 is defined between radiation source 32 and detector 36. In the exemplary embodiment, radiation source 32 and detector 36 are coupled to a gantry 40 for rotation about examination region 38. Alternatively, radiation source 32 and/or detector 36 are coupled within CT system 14 such that radiation source 32 and/or detector 36 are stationary with respect to examination region 38. In the exemplary embodiment, CT system 14 performs a continuous helical scan as stream 22 of objects 24 passes through examination region 38 unless conveyor 12 is halted, as described in more detail herein.

Radiation source 32 emits radiation 34 as X-rays in a cone-beam in the exemplary embodiment. Alternatively, radiation source 32 may emit any suitable radiation having any suitable beam shape, such as a fan beam. Detector 36 includes a plurality of rows 42 and columns (not shown) of detector elements 44. Each row 42 extends in a direction that is substantially perpendicular to a direction of object travel as indicated by directional arrow 46. The columns are substantially parallel to the object travel direction indicated by directional arrow 46. Each detector element 44 produces an electrical signal that represents an intensity of an impinging radiation beam and, hence, the attenuation of the beam as the beam passes through object 24. The electrical signals produced by detector elements 44 are transmitted to control system 26.

In the exemplary embodiment, a scan controller is in operative control communication with CT system 14. Control system 26 is in operational control communication with scan controller 48, which controls radiation source 32, detector 36, and gantry 40. Scan controller 48 controls emission of radiation 34 from radiation source 32 and receives data from detector 36. Scan controller 48 transmits data received from detector 36 to control system 26. Further, scan controller 48 controls components of CT system 14 in any suitable manner that enables CT system 14 to function as described herein.

Further, in the exemplary embodiment, a conveyor controller 50 is in operative control communication with conveyor 12. Control system 26 is in operational control communication with conveyor controller 50, which controls motion of conveyor 12. More specifically, conveyor controller 50 controls acceleration, deceleration, velocity, and/or any motion parameter of conveyor 12. Conveyor controller 50 receives commands from control system 26 to control conveyor 12, as described herein.

Figure 2:
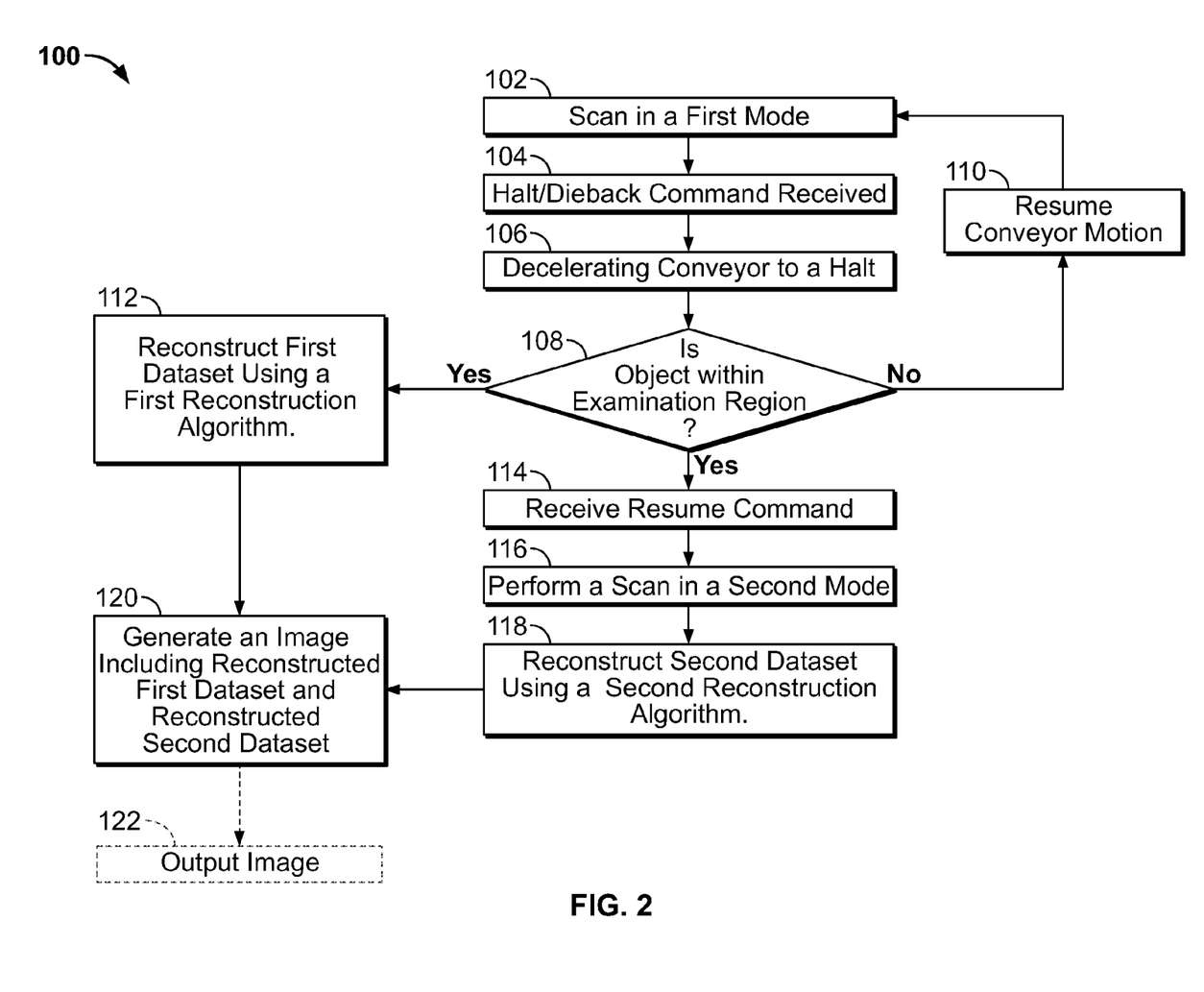
FIG. 2 is a flowchart of an exemplary method for performing a scan that may be used with the scanning system shown in FIG. 1.

FIG. 2 is a flowchart of an exemplary method 100 of performing a scan of an object 24 (shown in FIG. 1) that may be used with scanning system 10 (shown in FIG. 1). In the exemplary embodiment, method 100 is used when stream 22 of objects 24 (shown in FIG. 1) is being scanned by CT system 14 (shown in FIG. 1) using a continuous scan. In the exemplary embodiment, method 100 is performed by control system 26 (shown in FIG. 1), scan controller 48 (shown in FIG. 1), and conveyor controller 50 (shown in FIG. 1).

Referring to FIGS. 1 and 2, method 100 includes performing 102 a first portion of a scan in a first scanning mode to acquire a first dataset using scan controller 48. More specifically, the first portion of the scan in the first scanning mode is continuously performed 102 by scanning system 10 to acquire data of stream 22 of objects 24 as conveyor 12 transports objects 24 through CT system 14. During the first scanning mode, gantry 40 rotates about examination region 38, and conveyor 12 transports objects 24 through examination region 38.

The first portion of the scan in the first scanning mode is performed 102 until a halt command is issued by control system 26. More specifically, conveyor controller 50 receives 104 the halt command for conveyor 12 from control system 26. Further, scan controller 48 also receives 104 the halt command for gantry 40. The halt command instructs conveyor controller 50 to halt conveyor 12 and instructs scan controller 48 to stop acquiring image data of object 24.

Once conveyor controller 50 receives 104 the halt command, conveyor controller 50 decelerates 106 conveyor 12 from a motion during the first scanning mode to a halt based on the halt command. Control system 26 then determines 108 whether object 24 is present within examination region 38. More specifically, control system 26 determines 108 a presence of object 24 within examination region 38 using any suitable method and/or technique, such as using sensors within scanning system 10. When control system 26 determines 108 object 24 is not present within examination region 38, control system 26 commands conveyor controller 50 to resume 110 motion of conveyor 12. More specifically, conveyor 12 resumes 110 a motion for performing 102 the first scanning mode. After conveyor 12 resumes 110 motion, the first portion of the scan in the first scanning mode is performed 102. When control system 26 determines 108 object 24 is present within examination region 38, control system 26 reconstructs 112 the first dataset using a first reconstruction algorithm. However, in the exemplary embodiment, reconstruction 112 of the first dataset yields a partial image of object 24 within examination region 38.

Further, when control system 26 determines 108 object 24 is present within examination region 38, control system 26 issues a resume command. When scan controller 48 and/or conveyor controller 50 receives 114 the resume command, scan controller 48 and/or conveyor controller 50 perform 116 a second portion of the scan in a second scanning mode to acquire a second dataset. In the exemplary embodiment, the second scanning mode is different than the first scanning mode, and the first scanning mode and the second scanning mode are any suitable scanning modes.

After the scan in the second scanning mode is performed 116, control system 26 reconstructs 118 the second dataset using a second reconstruction algorithm. In the exemplary embodiment, the second reconstruction algorithm is different than the first reconstruction algorithm, and the first reconstruction algorithm and the second reconstruction algorithm are any suitable reconstruction algorithms. Reconstruction 118 of the second dataset yields another partial image of object 24. In the exemplary embodiment, the partial image from the first dataset reconstruction 112 and the partial image from the second dataset reconstruction 118 form a whole or complete image of object 24 within examination region 38.

More specifically, control system 26 generates 120 an image of object 24 using the first reconstructed dataset and the second reconstructed dataset. In the exemplary embodiment, the first reconstructed dataset and the second reconstructed dataset are combined to generate 120 the image. As such, a whole or complete image of object 24 is reconstructed even though motion of object 24 was halted and resumed during the continuous scan. The generated image is optionally output 122 to display device 30. The generated image may also be transmitted to any suitable system for further processing and/or inspection. In the exemplary embodiment, the generated image is used to determine contents of object 24. In a transportation setting, for example, such as at an airport, the generated image is used to determine if contraband, such as weapons, narcotics, explosives, and/or other prohibited materials or objects, is present within object 24. Method 100 is performed each time a halt command is received 104 during performance 102 of the first portion of scan in the first scanning mode.

Figure 3:
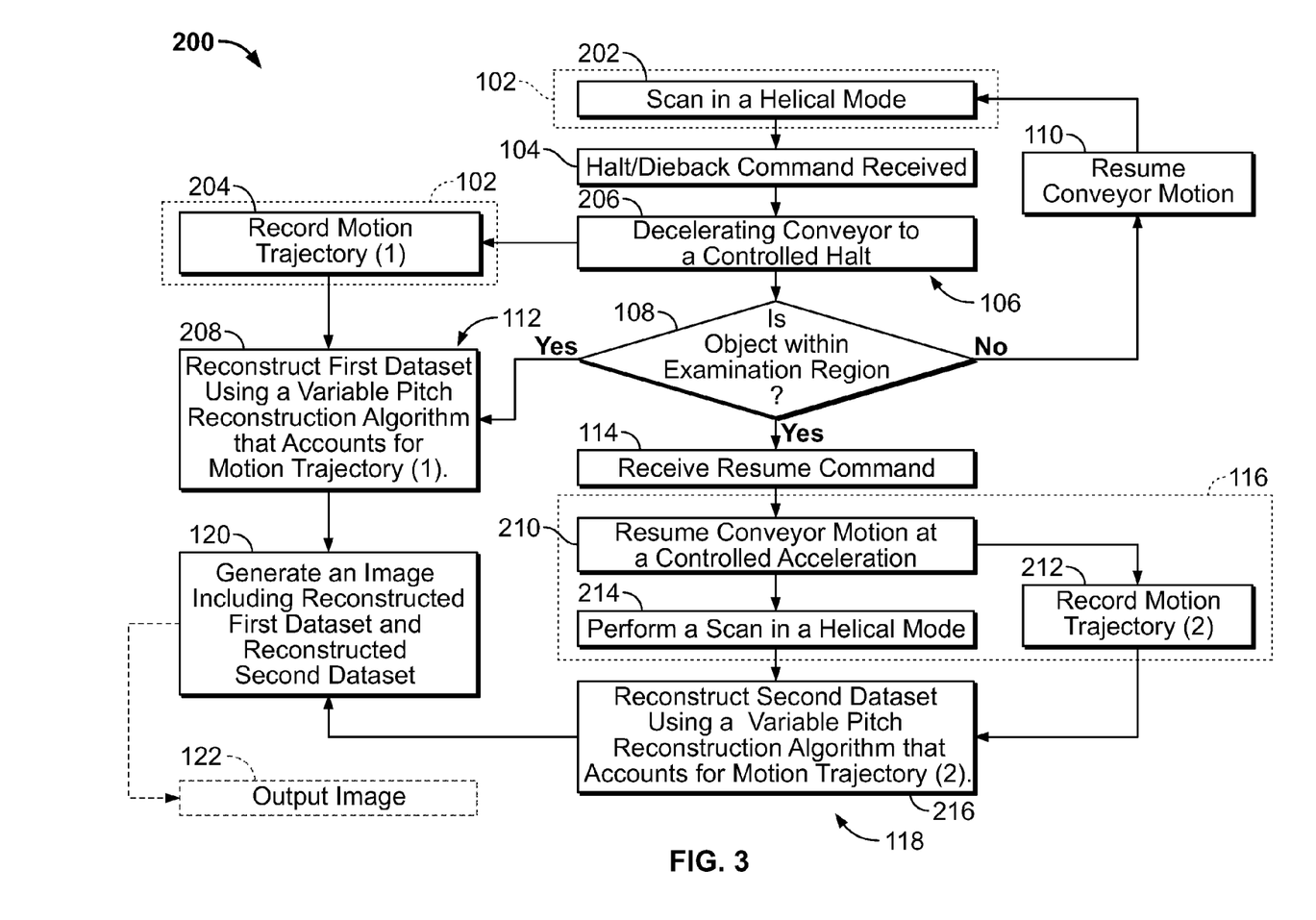
FIG. 3 is a flowchart of a first example of the method shown in FIG. 2.

FIG. 3 is a flowchart of a first example method 200 of method 100 (shown in FIG. 2). Method 200 includes the steps of method 100 and, as such, similar components are labeled with similar references.

Referring to FIGS. 1 and 3, method 200 includes performing 102 a first portion of a scan in a first scanning mode to acquire a first dataset using scan controller 48. More specifically, the first portion of the scan in the first scanning mode is continuously performed 102 by scanning system 10 to acquire data of stream 22 of objects 24 as conveyor 12 transports objects 24 through CT system 14. During the first scanning mode, gantry 40 rotates about examination region 38, and conveyor 12 transports objects 24 through examination region 38. In method 200, the first portion of the scan is performed 202 in a helical mode to acquire the first dataset. Performing 102 the first portion of the scan in the first scanning mode also includes recording 204 first motion trajectory data of conveyor 12 as conveyor 12 decelerates to a halt, as described in more detail below.

The first portion of the scan in the first scanning mode is performed 202 until a halt command is issued by control system 26. More specifically, conveyor controller 50 receives 104 the halt command for conveyor 12 from control system 26. Further, scan controller 48 also receives 104 the halt command for gantry 40. The halt command instructs conveyor controller 50 to halt conveyor 12 and instructs scan controller 48 to stop acquiring image data of object 24.

Once conveyor controller 50 receives 104 the halt command, conveyor controller 50 decelerates 106 conveyor 12 from a motion during the first scanning mode to a halt based on the halt command. More specifically, in method 200, deceleration 206 of conveyor 12 is controlled by controlling a rate of deceleration. The first portion of the scan in helical mode continues to be performed 202 while conveyor decelerates 206. A motion trajectory of conveyor 12 as conveyor 12 decelerates 206 is recorded 204 in control system 26 as part of the performance 102 of the first portion of the scan in the first scanning mode. More specifically, the motion trajectory, such as the rate of deceleration, is recorded 204 as the first motion trajectory data in control system 26.

Control system 26 then determines 108 whether object 24 is present within examination region 38. More specifically, control system 26 determines 108 the presence of object 24 within examination region 38 using any suitable method and/or technique, such as using sensors within scanning system 10. When control system 26 determines 108 object 24 is not present within examination region 38, control system 26 commands conveyor controller 50 to resume 110 motion of conveyor 12. More specifically, conveyor 12 resumes 110 a motion for performing 202 the first portion of the scan in the helical mode. After conveyor 12 resumes 110 motion, the first portion of the scan in the helical mode continues to be performed 202. When control system 26 determines 108 object 24 is present within examination region 38, control system 26 reconstructs 112 the first dataset using a first reconstruction algorithm. More specifically, method 200 includes reconstructing 208 the first dataset using a known variable pitch helical reconstruction algorithm that accounts for the recorded first motion trajectory data. One example of a known variable pitch helical reconstruction algorithm is the variable pitch helical reconstruction algorithm described in by Alexander Katsevich, Samit Basu, and Jiang Hsieh, "Exact filtered backprojection reconstruction for dynamic pitch helical cone beam computed tomography," 2004 Phys. Med. Biol. 49, pgs. 3089-3103 (referred to hereinafter as the "Katsevich algorithm"). However, in the exemplary embodiment, reconstruction 208 of the first dataset yields a partial image of object 24 within examination region 38.

Further, when control system 26 determines 108 object 24 is present within examination region 38, control system 26 issues a resume command. When scan controller 48 and/or conveyor controller 50 receives 114 the resume command, scan controller 48 and/or conveyor controller 50 perform 116 a second portion of the scan in a second scanning mode to acquire a second dataset. In the exemplary embodiment, the second scanning mode is different than the first scanning mode. The resume command in method 200 is transmitted to conveyor controller 50 to control the motion of conveyor 12 during the second scanning mode and is transmitted to scan controller 48 to control at least a motion of gantry 40.

More specifically, in method 200, performing 116 the second portion of the scan in the second scanning mode includes resuming 210 motion of conveyor 12 at a controlled acceleration, recording 212 second motion trajectory data of conveyor 12 as conveyor 12 accelerates, and performing 214 the second portion of the scan in a helical mode to acquire the second dataset. When resuming 210 motion of conveyor 12, conveyor controller 50 accelerates conveyor 12 from the halt after receiving 114 the resume command. Control system 26 records 212 data relating to the motion of conveyor 12 as the second motion trajectory data. The second motion trajectory data includes data related to acceleration of conveyor 12 and/or velocity of conveyor 12 before, during, and/or after the acceleration. In the exemplary embodiment, conveyor 12 accelerates to a velocity that is substantially equal to a velocity of conveyor 12 before the halt command was received 104. The second portion of the scan in helical mode is performed 214 while conveyor 12 accelerates and after conveyor 12 is at a substantially constant velocity.

After the second portion of the scan in the second scanning mode is performed 116, control system 26 reconstructs 118 the second dataset using a second reconstruction algorithm. In the exemplary embodiment, the second reconstruction algorithm is different than the first reconstruction algorithm. More specifically, in the exemplary embodiment, the second dataset is reconstructed 216 using a known variable pitch helical reconstruction algorithm that accounts for the recorded second motion trajectory data. One example of a known variable pitch helical reconstruction algorithm that can be used to reconstruct 216 the second dataset is the Katsevich algorithm. Reconstruction 216 of the second dataset yields another partial image of object 24. In the exemplary embodiment, the partial image from the first dataset reconstruction 208 and the partial image from the second dataset reconstruction 216 form a whole or complete image of object 24 within examination region 38.

More specifically, control system 26 generates 120 an image of object 24 using the first reconstructed dataset and the second reconstructed dataset. In the exemplary embodiment, the first reconstructed dataset and the second reconstructed dataset are combined to generate 120 the image. As such, a whole or complete image of object 24 is reconstructed even though motion of object 24 was halted and resumed during the continuous scan. The generated image is optionally output 122 to display device 30. The generated image may also be transmitted to any suitable system for further processing and/or inspection. In the exemplary embodiment, the generated image is used to determine contents of object 24. In a transportation setting, for example, such as at an airport, the generated image is used to determine if contraband, such as weapons, narcotics, explosives, and/or other prohibited materials or objects, is present within object 24. Method 200 is performed each time a halt command is received 104 during performance 102 of the first portion of the scan in the first scanning mode.

Figure 4:
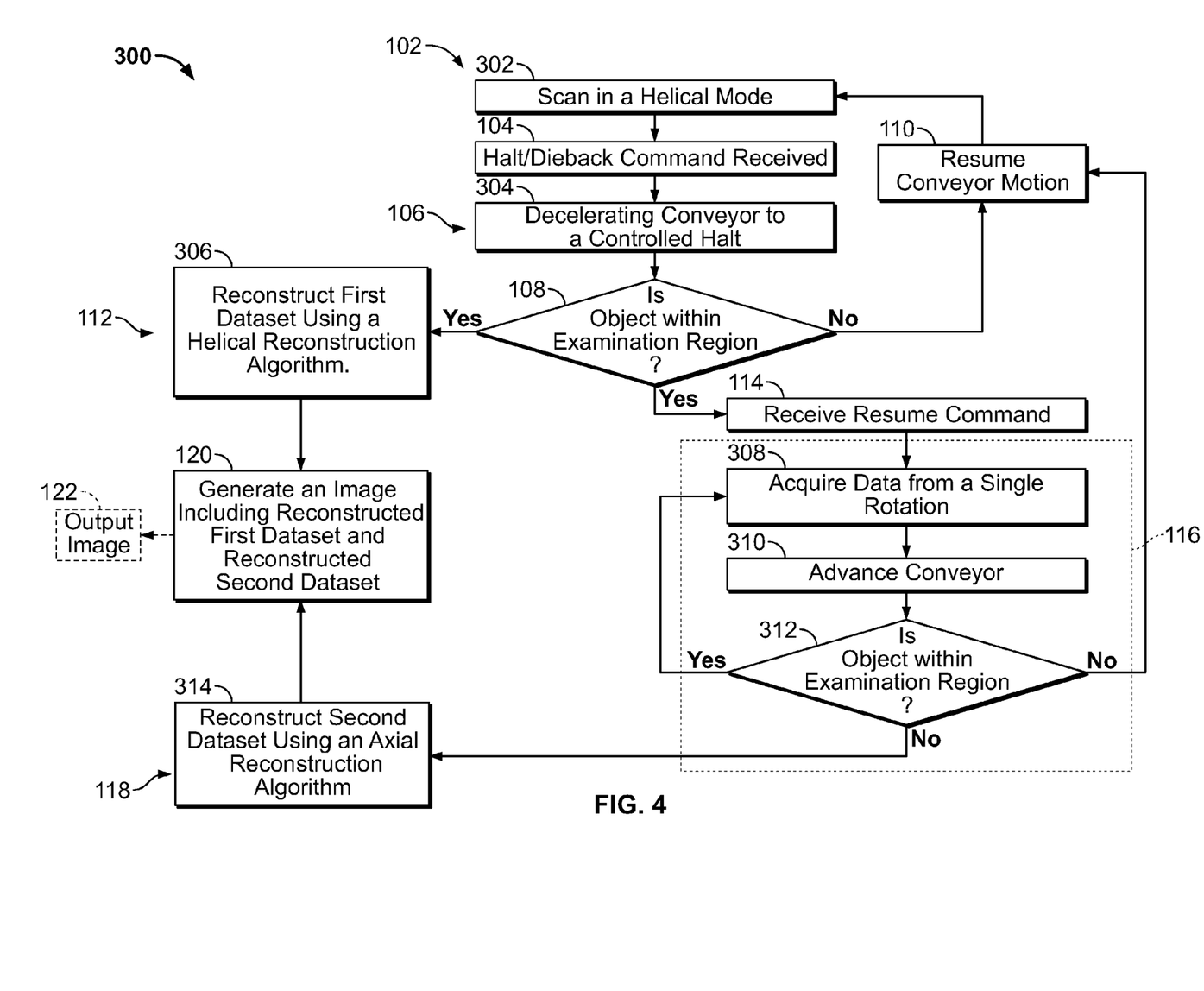
FIG. 4 is a flowchart of a second example of the method shown in FIG. 2.

FIG. 4 is a flowchart of a second example method 300 of method 100 (shown in FIG. 2). Method 300 includes the steps of method 100 and, as such, similar components are labeled with similar references.

Referring to FIGS. 1 and 4, method 300 includes performing 102 a first portion of a scan in a first scanning mode to acquire a first dataset using scan controller 48. More specifically, the first portion of the scan in the first scanning mode is continuously performed 102 by scanning system 10 to acquire data of stream 22 of objects 24 as conveyor 12 transports objects 24 through CT system 14. During the first scanning mode, gantry 40 rotates about examination region 38, and conveyor 12 transports objects 24 through examination region 38. In method 300, the first portion of the scan is performed 302 in a helical mode to acquire the first dataset.

The first portion of the scan in helical mode is performed 302 until a halt command is issued by control system 26. More specifically, conveyor controller 50 receives 104 the halt command for conveyor 12 from control system 26. Further, scan controller 48 also receives 104 the halt command for gantry 40. The halt command instructs conveyor controller 50 to halt conveyor 12 and instructs scan controller 48 to stop acquiring image data of object 24.

Once conveyor controller 50 receives 104 the halt command, conveyor controller 50 decelerates 106 conveyor 12 from a motion during the first scanning mode to a halt based on the halt command. More specifically, method 300 includes decelerating 304 conveyor 12 at a controlled rate of deceleration. Control system 26 then determines 108 whether object 24 is present within examination region 38. More specifically, control system 26 determines 108 a presence of object 24 within examination region 38 using any suitable method and/or technique, such as using sensors within scanning system 10. When control system 26 determines 108 object 24 is not present within examination region 38, control system 26 commands conveyor controller 50 to resume 110 motion of conveyor 12. More specifically, conveyor 12 resumes 110 a motion for performing 302 the first scanning mode. After conveyor 12 resumes 110 motion, the first portion of the scan in the helical mode is performed 302. When control system 26 determines 108 object 24 is present within examination region 38, control system 26 reconstructs 112 the first dataset using a first reconstruction algorithm.

More specifically, in method 300, the first dataset is reconstructed 306 using a known helical reconstruction algorithm, such as a three-dimensional helical reconstruction algorithm. Examples of algorithms that can be used to perform reconstruction 306 are the algorithm described in World Intellectual Property Organization published application No. WO 08/036463 A2, "Ray Consistency Based Reconstruction of Helical Cone Beam Data," (hereinafter referred to as the "Pack algorithm") and the algorithm described in U.S. Pat. No. 6,574,299, "Exact filtered back projection (FBP) algorithm for spiral computer tomography," to Alexander Katsevich (hereinafter referred to as the "Exact FBP algorithm"). However, in the exemplary embodiment, reconstruction 306 of the first dataset yields a partial image of object 24 within examination region 38.

Further, when control system 26 determines 108 object 24 is present within examination region 38, control system 26 issues a resume command. When scan controller 48 and/or conveyor controller 50 receives 114 the resume command, scan controller 48 and/or conveyor controller 50 perform 116 a second portion of the scan in a second scanning mode to acquire a second dataset. In the exemplary embodiment, the second scanning mode is different than the first scanning mode. The resume command in method 300 is transmitted to conveyor controller 50 to control the motion of conveyor 12 during the second scanning mode and is transmitted to scan controller 48 to control at least a motion of gantry 40. More specifically, in the exemplary embodiment, the second scanning mode is a step-and-shoot mode. Performing 116 the second portion of the scan in the second scanning mode includes acquiring 308 data from a single rotation of gantry 40 about examination region 38 and advancing 310 conveyor 12 by a predetermined amount using conveyor controller 50. The predetermined amount is selected to scan a subsequent portion of object 24 using another single rotation of gantry 40.

After conveyor 12 is advanced 310 by control system 26 and conveyor controller 50, control system 26 determines 312 whether object 24 is within examination region 38 using any suitable method and/or technique. When control system 26 determines 312 that object 24 is present within examination region 38, control system 26 acquires 308 data from a subsequent single rotation of gantry 40 via scan controller 48, and again advances 310 conveyor 12 via conveyor controller 50.

When control system 26 determines 312 object 24 is not present within examination region 38, control system 26 commands conveyor controller 50 to resume 110 motion of conveyor 12. More specifically, conveyor 12 resumes 110 a motion for performing 302 the first scanning mode. Further, when control system 26 determines 312 object 24 is not present within examination region 38, control system 26 reconstructs 118 the second dataset using a second reconstruction algorithm. In the exemplary embodiment, the second reconstruction algorithm is different than the first reconstruction algorithm. More specifically, in the exemplary embodiment, control system 26 reconstructs 314 the second dataset using a known axial reconstruction algorithm. One example of an algorithm used to perform reconstruction 314 is the algorithm described by L. A. Feldkamp, L. C. Davis, and J. W. Kreiss, "Practical Cone Beam Algorithms." J of Opt. Soc. Am., A/Vol. 1, No. 6, pgs. 612-619 (June 1984) (hereinafter referred to as the "FDK algorithm"). Reconstruction 314 of the second dataset yields another partial image of object 24. In the exemplary embodiment, the partial image from the first dataset reconstruction 306 and the partial image from the second dataset reconstruction 314 form a whole or complete image of object 24 within examination region 38.

More specifically, control system 26 generates 120 an image of object 24 using the first reconstructed dataset and the second reconstructed dataset. In the exemplary embodiment, the first reconstructed dataset and the second reconstructed dataset are combined to generate 120 the image. As such, a whole or complete image of object 24 is reconstructed even though motion of object 24 was halted and resumed during the continuous scan. The generated image is optionally output 122 to display device 30. The generated image may also be transmitted to any suitable system for further processing and/or inspection. In the exemplary embodiment, the generated image is used to determine contents of object 24. In a transportation setting, for example, such as at an airport, the generated image is used to determine if contraband, such as weapons, narcotics, explosives, and/or other prohibited materials or objects, is present within object 24. Method 300 is performed each time a halt command is received 104 during performance 102 of the scan in the first scanning mode.

Figure 5:
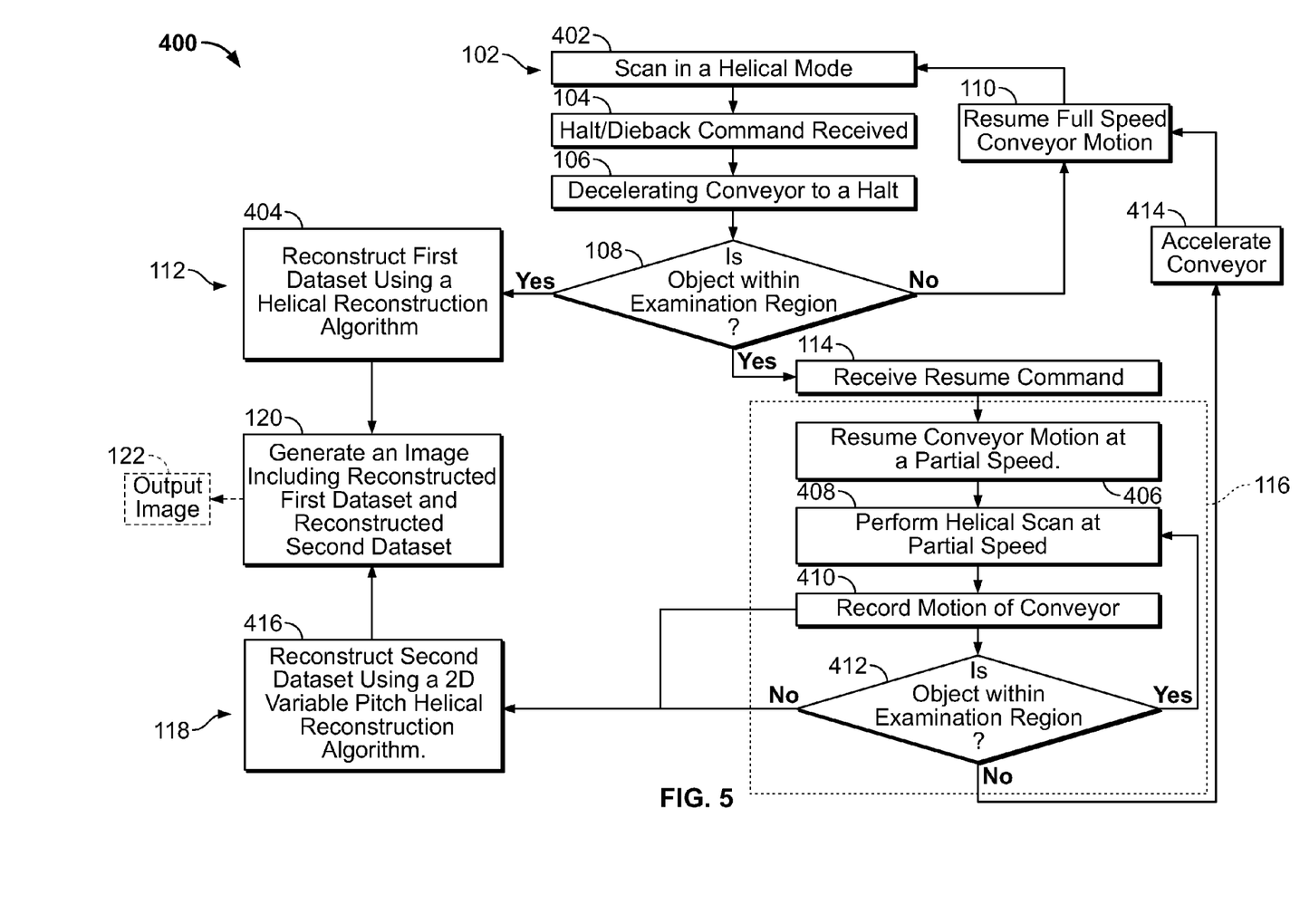
FIG. 5 is a flowchart of a third example of the method shown in FIG. 2.

FIG. 5 is a flowchart of a third example method 400 of method 100 (shown in FIG. 2). Method 400 includes the steps of method 100 and, as such, similar components are labeled with similar references.

Referring to FIGS. 1 and 5, method 400 includes performing 102 a first portion of a scan in a first scanning mode to acquire a first dataset using scan controller 48. More specifically, the first portion of the scan in the first scanning mode is continuously performed 102 by scanning system 10 to acquire data of stream 22 of objects 24 as conveyor 12 transports objects 24 through CT system 14. During the first scanning mode, gantry 40 rotates about examination region 38, and conveyor 12 transports objects 24 through examination region 38. In method 400, the first portion of the scan is performed 402 in a helical mode at a first speed to acquire the first dataset. The scan performed 402 at the first speed is also referred to herein as a "full speed scan." As used herein, the term "speed" refers to at least a velocity of conveyor 12 through scanning system 10. The term "speed" may also refer to a rotational velocity of gantry 40.

The first portion of the scan in helical mode is performed 402 until a halt command is issued by control system 26. More specifically, conveyor controller 50 receives 104 the halt command for conveyor 12 from control system 26. Further, scan controller 48 also receives 104 the halt command for gantry 40. The halt command instructs conveyor controller 50 to halt conveyor 12 and instructs scan controller 48 to stop acquiring image data of object 24.

Once conveyor controller 50 receives 104 the halt command, conveyor controller 50 decelerates 106 conveyor 12 from a motion during the first scanning mode to a halt based on the halt command. Control system 26 then determines 108 whether object 24 is present within examination region 38. More specifically, control system 26 determines 108 a presence of object 24 within examination region 38 using any suitable method and/or technique, such as using sensors within scanning system 10. When control system 26 determines 108 object 24 is not present within examination region 38, control system 26 commands conveyor controller 50 to resume 110 motion of conveyor 12. More specifically, conveyor 12 resumes 110 a motion for performing 402 the first scanning mode such that the first portion of the scan is performed 402 at the first speed. After conveyor 12 resumes 110 motion, the first portion of the scan in the full speed helical mode is performed 402. When control system 26 determines 108 object 24 is present within examination region 38, control system 26 reconstructs 112 the first dataset using a first reconstruction algorithm. More specifically, in method 400, the first dataset is reconstructed 404 using a known helical reconstruction algorithm, such as a three-dimensional helical reconstruction algorithm. Examples of algorithms that can be used to perform reconstruction 404 are the Pack algorithm and the Exact FBP algorithm. However, in the exemplary embodiment, reconstruction 404 of the first dataset yields a partial image of object 24 within examination region 38.

Further, when control system 26 determines 108 object 24 is present within examination region 38, control system 26 issues a resume command. When scan controller 48 and/or conveyor controller 50 receives 114 the resume command, scan controller 48 and/or conveyor controller 50 perform 116 a second portion of the scan in a second scanning mode to acquire a second dataset. In the exemplary embodiment, the second scanning mode is different than the first scanning mode. The resume command in method 400 is transmitted to conveyor controller 50 to control the motion of conveyor 12 during the second scanning mode and is transmitted to scan controller 48 to control at least a motion of gantry 40. More specifically, in the exemplary embodiment, the second scanning mode is a helical scan mode at a second speed that is less than the first speed. The second portion of the scan performed 408 at the second speed is also referred to herein as a "partial speed scan." Performing 116 the second portion of the scan in the second scanning mode includes resuming 406 motion of conveyor 12 at the second speed, performing 408 a helical scan at the second speed, and recording 410 motion data of conveyor 12 as the helical scan is performed 408. In the exemplary embodiment, the recorded motion data of conveyor 12 includes acceleration data and/or speed data.

As the helical scan at the second speed is performed 408, control system 26 determines 412 whether object 24 is within examination region 38 using any suitable method and/or technique. When control system 26 determines 412 that object 24 is present within examination region 38, control system 26 continues to perform 408 the helical scan at the second speed to acquire data via CT system 14 and continues to record 410 the motion of conveyor 12.

When control system 26 determines 412 object 24 is not present within examination region 38, control system 26 commands conveyor controller 50 to resume 110 motion of conveyor 12 at the first speed. More specifically, conveyor 12 resumes 110 a motion for performing 402 the first scanning mode. To resume 110 the first speed, control system 26 accelerates 414 conveyor 12 to the speed of the first helical mode using conveyor controller 50 when object 24 has exited examination region 38. After conveyor 12 resumes 110 motion at the first speed, the first portion of the scan is performed 102. Further, when control system 26 determines 412 object 24 is not present within examination region 38, control system 26 reconstructs 118 the second dataset using a second reconstruction algorithm. In the exemplary embodiment, the second reconstruction algorithm is different than the first reconstruction algorithm. More specifically, in the exemplary embodiment, control system 26 reconstructs 416 the second dataset using a known two-dimensional variable pitch helical reconstruction algorithm. An example of an algorithm that can be used to perform reconstruction 416 is the algorithm described in U.S. Pat. No. 6,411,670, "Data Rebinning to Increase Resolution in CT Image Reconstruction" (hereinafter referred to as the "Besson algorithm"). Reconstruction 416 of the second dataset yields another partial image of object 24. In the exemplary embodiment, the partial image from the first dataset reconstruction 404 and the partial image from the second dataset reconstruction 416 form a whole or complete image of object 24 within examination region 38.

More specifically, control system 26 generates 120 an image of object 24 using the first reconstructed dataset and the second reconstructed dataset. In the exemplary embodiment, the first reconstructed dataset and the second reconstructed dataset are combined to generate 120 the image. As such, a whole or complete image of object 24 is reconstructed even though motion of object 24 was halted and resumed during the continuous scan. The generated image is optionally output 122 to display device 30. The generated image may also be transmitted to any suitable system for further processing and/or inspection. In the exemplary embodiment, the generated image is used to determine contents of object 24. In a transportation setting, for example, such as at an airport, the generated image is used to determine if contraband, such as weapons, narcotics, explosives, and/or other prohibited materials or objects, is present within object 24. Method 400 is performed each time a halt command is received 104 during performance 102 of the first portion of the scan in the first scanning mode.

The above-described embodiments facilitate continuously scanning a stream of objects even when the stream of objects halts and resumes motion. More specifically, the embodiments described herein enable an object to continue to be scanned after the object has halted in an imaging section of a scanning system while a scan is being performed. Data acquired before the object is halted is not discarded and is used to reconstruct an image of the object. As such, the object is not required to be manually inspected when a halt within the imaging section occurs. Further, the second implementation of the exemplary method described herein facilitates maintaining a quality of the image after a halt has occurred. The above-described the third implementation of the exemplary method facilitates resuming a full speed scan after a halt because a conveyor continues to move through a second scanning mode.

A technical effect of the systems and method described herein includes at least one of: (a) performing a first portion of a scan in a first scanning mode to acquire a first dataset using a scan controller; (b) receiving a halt command for a conveyor within a scanning system at at least a conveyor controller; (c) decelerating a conveyor to a halt based on a halt command using a conveyor controller; (d) when an object is present within an examination region after a conveyor has halted, performing a second portion of a scan in a second scanning mode to acquire a second dataset using a scan controller, the second scanning mode different than a first scanning mode; (e) reconstructing a first dataset using a first reconstruction algorithm within a control system; (f) reconstructing a second dataset using a second reconstruction algorithm within a control system, the second reconstruction algorithm different than a first reconstruction algorithm; and (g) generating an image using a first reconstructed dataset and a second reconstructed dataset using a control system.

Exemplary embodiments of a method and a system for performing a scan of an object are described above in detail. The method and system are not limited to the specific embodiments described herein, but rather, components of the system and/or steps of the method may be utilized independently and separately from other components and/or steps described herein. For example, the method may also be used in combination with other scanning systems and methods, and is not limited to practice with only the computer tomography system and methods as described herein. Rather, the exemplary embodiment can be implemented and utilized in connection with many other imaging applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A method for generating an image of an object using a scanning system, said method comprising:
   performing a first portion of a scan in a first scanning mode to acquire a first dataset using a scan controller;
   receiving a halt command for a conveyor within the scanning system at at least a conveyor controller;
   decelerating the conveyor to a halt based on the halt command using the conveyor controller;
   when the object is present within an examination region after the conveyor has halted, performing a second portion of the scan in a second scanning mode to acquire a second dataset using the scan controller, the second scanning mode different than the first scanning mode;
   reconstructing the first dataset using a first reconstruction algorithm within a control system;
   reconstructing the second dataset using a second reconstruction algorithm within the control system, the second reconstruction algorithm different than the first reconstruction algorithm; and
   generating the image using the first reconstructed dataset and the second reconstructed dataset using the control system.

2. A method in accordance with claim 1, wherein performing a first portion of a scan in a first scanning mode to acquire a first dataset comprises:
   performing the first portion of the scan in a helical mode to acquire the first dataset; and
   recording first motion trajectory data of the conveyor within the control system as the conveyor decelerates to the halt.

3. A method in accordance with claim 2, wherein reconstructing the first dataset using a first reconstruction algorithm comprises reconstructing the first dataset using a variable pitch helical reconstruction algorithm that accounts for the recorded first motion trajectory data.

4. A method in accordance with claim 2, wherein performing a second portion of the scan in a second scanning mode to acquire a second dataset comprises:
   performing the second portion of the scan in a helical mode to acquire the second dataset; and
   recording second motion trajectory data of the conveyor within the control system as the conveyor accelerates.

5. A method in accordance with claim 4, wherein reconstructing the second dataset using a second reconstruction algorithm comprises reconstructing the second dataset using a variable pitch helical reconstruction algorithm that accounts for the recorded second motion trajectory data.

6. A method in accordance with claim 1, wherein performing a first portion of a scan in a first scanning mode to acquire a first dataset comprises performing the first portion of the scan in a first helical mode.

7. A method in accordance with claim 6, wherein reconstructing the first dataset using a first reconstruction algorithm comprises reconstructing the first dataset using a three-dimensional helical reconstruction algorithm.

8. A method in accordance with claim 6, wherein performing a second portion of the scan in a second scanning mode to acquire a second dataset comprises performing the second portion of the scan in a step-and-shoot mode.

9. A method in accordance with claim 8, wherein reconstructing the second dataset using a second reconstruction algorithm comprises reconstructing the second dataset using an axial reconstruction algorithm.

10. A method in accordance with claim 6, wherein performing a second portion of the scan in a second scanning mode to acquire a second dataset comprises:
    performing the second portion of the scan in second helical mode, the second helical mode performed at a speed slower than a speed at which the first helical mode is performed; and
    recording motion data of the conveyor during the second helical mode within the control system.

11. A method in accordance with claim 10, wherein reconstructing the second dataset using a second reconstruction algorithm comprises reconstructing the second dataset using a two-dimensional variable pitch helical reconstruction algorithm.

12. A method in accordance with claim 10, further comprising accelerating the conveyor to the speed at which the first helical mode is performed using the conveyor controller when the object has exited the examination region.

13. A method in accordance with claim 1, further comprising:
    after receiving the halt command, determining if the object is present within the examination region using the control system;
    when the object is present within the examination region, receiving a resume command at at least one of the conveyor controller and the scan controller, the resume command instructing the scanning system to perform the second portion of the scan in the second scanning mode; and
    when the object is not present within the examination region, resuming a motion of the conveyor for performing the first portion of the scan in the first scanning mode using the conveyor controller.

14. A scanning system, comprising:
    a conveyor configured to convey a stream of objects through said scanning system;
    a conveyor controller in operative control communication with said conveyor;
    a computer tomography (CT) system;
    a scan controller in operative control communication with said CT system; and
    a control system in communication with said conveyor controller and said scan controller, said control system configured to:
        perform a first portion of a scan in a first scanning mode to acquire a first dataset using said scan controller;
        issue a halt command to at least said conveyor controller;
        decelerate said conveyor to a halt based on the halt command using said conveyor controller;
        when an object is present within an examination region after said conveyor has halted, perform a second portion of the scan in a second scanning mode to acquire a second dataset using said scan controller, the second scanning mode different than the first scanning mode;

reconstruct the first dataset using a first reconstruction algorithm;

reconstruct the second dataset using a second reconstruction algorithm, the second reconstruction algorithm different than the first reconstruction algorithm; and generate an image using the first reconstructed dataset and the second reconstructed dataset.

15. A scanning system in accordance with claim 14, wherein at least one of said conveyor controller and said scan controller is configured to:

perform the first portion of the scan in a first helical mode;

record first trajectory data during the first portion of the scan in the first helical mode;

receive the halt command;

perform the second portion of the scan in a second helical mode; and record second trajectory data during the second portion of the scan in the second helical mode.

16. A scanning system in accordance with claim 15, wherein said control system is configured to:

reconstruct data acquired during the first portion of the scan using a variable pitch helical reconstruction algorithm that accounts for the recorded first motion trajectory data; and reconstruct data acquired during the second portion of the scan using a variable pitch helical reconstruction algorithm that accounts for the recorded second motion trajectory data.

17. A scanning system in accordance with claim 14, wherein at least one of said conveyor controller and said scan controller is configured to:

perform the first portion of the scan in a helical scan mode;

receive the halt command; and perform the second portion of the scan in a step-and-shoot scan mode.

18. A scanning system in accordance with claim 17, wherein said control system is configured to:

reconstruct data acquired during the first portion of the scan in the helical scan mode using a helical reconstruction algorithm; and reconstruct data acquired during the second portion of the scan in the step-and-shoot scan mode using an axial reconstruction algorithm.

19. A scanning system in accordance with claim 14, wherein at least one of said conveyor controller and said scan controller is configured to:

perform the first portion of the scan in a helical scan mode at a first speed;

receive the halt command; and perform the second portion of the scan in a helical scan mode at a second speed.

20. A scanning system in accordance with claim 19, wherein said control system is configured to:

reconstruct data acquired during the first portion of the scan in the helical scan mode at the first speed using a helical reconstruction algorithm; and reconstruct data acquired during the second portion of the scan in the helical scan mode at the second speed using a two-dimensional variable pitch helical reconstruction algorithm.

* * * * *